(12) United States Patent
Wang et al.

(10) Patent No.: US 10,214,478 B2
(45) Date of Patent: Feb. 26, 2019

(54) AMANTADINE NITRATE COMPOUNDS WITH NEURAL PROTECTIVE EFFECT, AND PREPARATION AND MEDICAL USE THEREOF

(71) Applicant: GUANGZHOU MAGPIE PHARMACEUTICALS CO., LTD., Guangzhou (CN)

(72) Inventors: Yuqiang Wang, Guangzhou (CN); Zheng Liu, Guangzhou (CN); Pei Yu, Guangzhou (CN); Yewei Sun, Guangzhou (CN); Zaijun Zhang, Guangzhou (CN); Gaoxiao Zhang, Guangzhou (CN); Luchen Shan, Guangzhou (CN); Peng Yi, Guangzhou (CN); James Larrick, Woodside, CA (US)

( * ) Notice: Subject to any disclaimer, the term of this patent is extended or adjusted under 35 U.S.C. 154(b) by 0 days.

(21) Appl. No.: 15/530,054

(22) Filed: Nov. 28, 2016

(65) Prior Publication Data

US 2018/0148404 A1    May 31, 2018

(51) Int. Cl.
*C07C 211/38* (2006.01)
*A61P 25/00* (2006.01)

(52) U.S. Cl.
CPC ............ *C07C 211/38* (2013.01); *A61P 25/00* (2018.01); *C07C 2603/74* (2017.05)

(58) Field of Classification Search
CPC .................................................... C07C 211/38
USPC ......................................................... 514/662
See application file for complete search history.

(56) References Cited

U.S. PATENT DOCUMENTS 7,326,730 B2 * 2/2008 Wang .................... C07C 219/24
514/511

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin A Vajda
(74) *Attorney, Agent, or Firm* — Charles Liu

(57) ABSTRACT

The present invention relates to amantadine nitrate compounds having neural protective effect, and preparation method and medical use thereof. The compounds have the structure of the general formula (I).

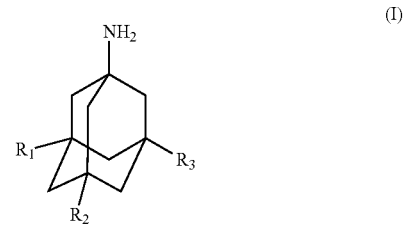

The compounds have multifunctional mechanisms, including inhibiting NMDA receptors, releasing NO, inhibiting calcium influxes, and having protective effects on cells particularly neurocytes. The compounds can be used in the preparation of medicaments having a cellular protective effect, for prevention or treatment of the diseases related to such as NMDA receptors and elevation of calcium anions in cells, including the diseases related to neurodegeneration such as Alzheimer's disease, Parkinson's disease, cerebral paralysis and glaucoma, and the diseases related to cardio-cerebral-vascular system such as Parkinson's syndrome combined with cerebral arteriosclerosis, as well as respiratory tract infections caused by influenza virus.

6 Claims, 4 Drawing Sheets

Reagents and conditions: (a) fuming HNO₃, Ac₂O, CH₂Cl₂; (b) HCl, ether.

Reagents and conditions: (a) HCOOH, n-Hexane, H₂SO₄; (b) CH₃CN, H₂SO₄; (c) ClCOOC₂H₅, TEA, NaBH₄; (d) NaOH, diethylene glycol, 170 °C, 15 h; (e) (Boc)₂O, Et₃N, CH₂Cl₂, 5 h; (f) Ac₂O, fuming HNO₃; (g) HCl, ether.

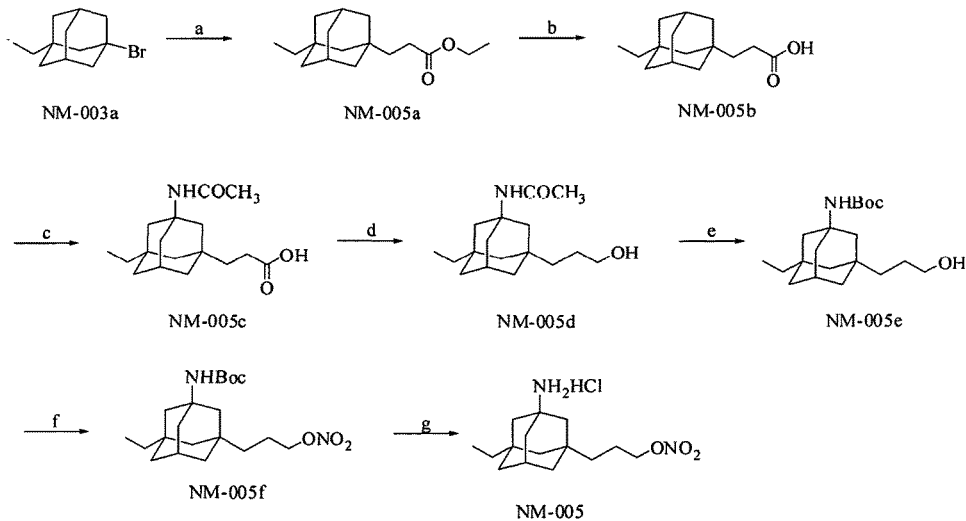

Reagents and conditions: (a) Ethyl acrylate, AIBN, n-Bu₃SnH, Toluene, 110 °C, 2 h; (b) KOH, MeOH/H₂O, rt, overnight; (c) CH₃CN, HNO₃,H₂SO₄; (d) ClCOOC₂H₅, Et₃N, THF, NaBH₄; (e) NaOH, Diethylene glycol, 170 °C, 15 h; (f) (Boc)₂O, Et₃N, CH₂Cl₂, 5 h; (g) fuming HNO₃, Ac₂O, CH₂Cl₂; (g) HCl, ethyl.

FIG.3

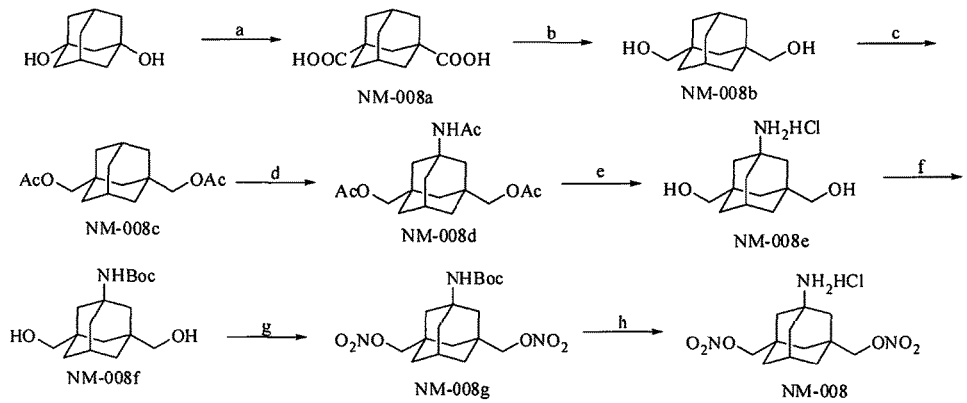

Reagents and conditions: (a) HCOOH, H₂SO₄, 3 h; (b) ClCOOC₂H₅, TEA, NaBH₄; (c) Ac₂O, HClO₄; (d) CH₃CN, H₂SO₄; (e) 18% HCl, 48 h; (f) DMF, (BOC)₂O, TEA, DMAP, 5 h; (g) Ac₂O, fuming HNO₃, CH₂Cl₂; (h) HCl, ether.

FIG.4

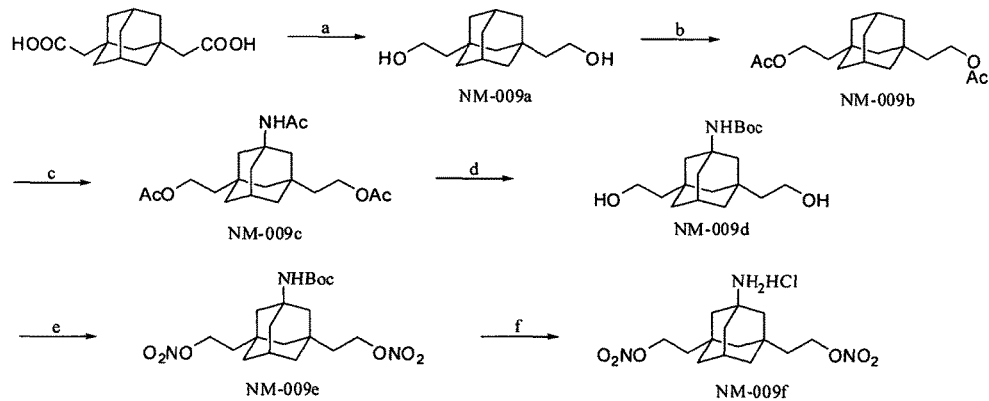

Reagents and conditions: (a) ClCOOC$_2$H$_5$, TEA, NaBH$_4$; (b) Ac$_2$O, HClO$_4$; (c) CH$_3$CN, H$_2$SO$_4$; (d) NaOH, Diethylene glycol, 170 °C, 15 h; (e) (BOC)$_2$O, TEA, THF, 5 h; (f) Ac$_2$O, fuming HNO$_3$,CH$_2$Cl$_2$; (g) HCl, ether.

FIG.5

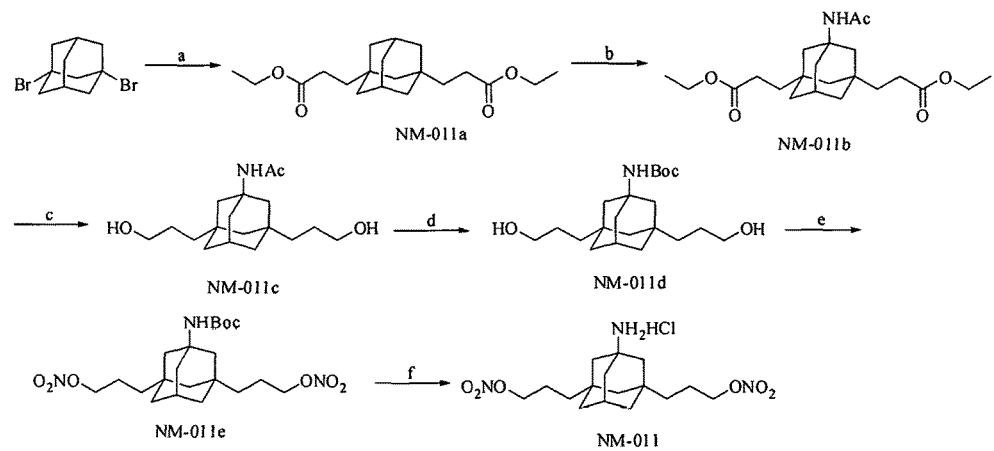

Reagents and conditions: (a) Ethyl acrylate, AIBN, n-Bu$_3$SnH, Toluene, 110 °C, 2 h; (b) CH$_3$CN, HNO$_3$,H$_2$SO$_4$; (c) NaBH$_4$, AlCl$_3$, THF; (d) (1)NaOH, Diethylene glycol, 170 °C, 15 h; (2) (Boc)$_2$O, Et$_3$N, CH$_2$Cl$_2$, 5 h; (e) fuming HNO$_3$, Ac$_2$O, CH$_2$Cl$_2$; (g)HCl, ethyl.

FIG.6

Reagents and conditions: (a) Ethyl methacrylate, AIBN, n-Bu$_3$SnH, Toluene, 110 °C, 2 h; (b) CH$_3$CN, HNO$_3$,H$_2$SO$_4$; (c) NaBH$_4$, AlCl$_3$, THF; (d) (1)NaOH, Diethylene glycol, 170 °C, 15 h; (2) (Boc)$_2$O, Et$_3$N, CH$_2$Cl$_2$, 5 h; (e) fuming HNO$_3$, Ac$_2$O, CH$_2$Cl$_2$; (g)HCl, ethyl.

AMANTADINE NITRATE COMPOUNDS WITH NEURAL PROTECTIVE EFFECT, AND PREPARATION AND MEDICAL USE THEREOF

FIELD OF THE INVENTION

The present invention relates to medical field and, more particularly, to amantadine derivatives with neural protective effect, and methods for preparation thereof and uses thereof for manufacture of medicaments and for prevention and treatment of diseases.

BACKGROUND OF THE INVENTION

Amantadine and its derivatives with various biological activities have been widely used in the medical field. Rimantadine (1-aminoethyl adamantane) is currently used in medicaments for the prevention and treatment of influenza. Amantadine is widely used in the treatment of influenza and Parkinson's disease (PD) (Schwab et al., *J. Am. Med. Assoc.* 1969, 208: 1168). Memantine (1,3-dimethyl adamantane) currently is used as the only NMDA receptor antagonist proved by FDA to be used for the treatment of moderate to severe Alzheimer's Disease (AD). The NMDA receptor is an important subtype of excitatory amino acid ionic glutamate receptors in central nervous system, and is also an important receptor related to the learning and memory processes. When the NMDA receptor channel is opened, some cations, such as $Ca^{2+}$, $K^+$ and $Na^+$ maybe allowed unselectively to enter into the cells, and the entry of such ions, especially calcium ions, may cause a series of biochemical reactions, which may induce neurotoxicity and eventually cause neuronal apoptosis. Memantine is a noncompetitive antagonist of the NMDA receptor open-channel, and it can combine with the binding sites in the ion channel to block the ion flow and thus has neuro-protective effect. The combination of memantine to NMDA receptor is reversible with a moderate rate of dissociation, which may ensure the pharmacological effects and on the other hand may prevent the channel from being blocked for normal physiological functions (Lipton et al., Journal of Neurochemistry 2006, 97: 1611-1626). Meanwhile, memantine has a strong voltage dependence to the antagonism of the NMDA receptor and can bind to the receptor only under neuronal depolarization, and thus can block the activation of the NMDA receptor as neurons being continually polarized in pathological conditions, but does not block the activation of the NMDA receptor in normal physiological conditions (Wenk et al, CNS Drug Reviews 2003, 9 (3): 275-308; McKeage, Drugs & Aging 2010, 27 (2): 177-179). Such protection mechanism also has important significance for the treatment of other disorders of central nervous system, such as stroke, PD and ALS.

Nitric oxide (NO) also has a variety of biological activities in the body, and has a function of signaling molecules. Nitric oxide molecules can penetrate the cell wall into the smooth muscle cells to relax the cells, dilate blood vessels, and lower blood pressure. NO molecules can also enter into platelet cells and reduce their activities, and thus can inhibit the cells' aggregation and adhesion to the vascular endothelium, and further prevent thrombosis and atherosclerosis. Nitric oxide, as a free radical gas with an unpaired electron, is very unstable in the body and can easily react with free radicals, and thus can reduce the number of free radicals. The accumulation of free radicals can cause rupture of nucleic acids, inactivation of enzymes, depolymerization of polysaccharides, and peroxidation of lipids, and eventually may cause the neuronal death (Yan et al Free Radic Biol Med 2013, 62: 90-101). NO has very high activity towards various of radicals, and can effectively reduce the number of free radicals, however, it's synthesis in the body requires nitric oxide synthase (NOS). Under normal conditions, NOS has relatively low activity, and needs to be activated with nitro molecules or saponins. Introduction of a NO releasing group in a small molecule drug, such as in nitroglycerin, may increase NO content in the body, and thus may significantly enhance the therapeutic effect.

As the pathogenesis of AD is rather complex, currently available methods for clinical treatment of AD are very limited; there are only four kinds of acetylcholine esterase inhibitors and one NMDA receptor inhibitor. Such drug molecules with single target function may only relieve some clinical symptoms but cannot actually cure the disease of AD and thus cannot block the neurodegenerative process.

SUMMARY OF THE INVENTION

The present invention is directed to provide amantadine nitrate compounds of multifunctional targets and having neural protective effects. Of these compounds, multiple pharmacophores with specific targets were incorporated into the same molecule on the basis of drug design theories of pharmacophores, such that the compounds may have functions of inhibiting NMDA, releasing NO, inhibiting calcium influxes, removing radicals and neuro-protection. These compounds, which have multiple mechanisms, can be used to improve efficacy and reduce toxicity and side effects associated with combination therapy.

The present invention is also directed to provide a method of preparation of the amantadine nitrate compounds having neural protective effects.

The present invention is further directed to provide uses of the amantadine nitrate compounds with neural protective effects in the manufacture of medicaments.

The compounds of the invention have a structure of formula (I):

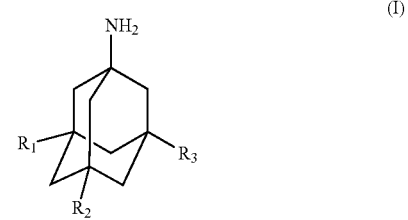

wherein, $R_1$, $R_2$ and $R_3$ are each independently hydrogen, straight-chain or branched-chain alkyl, optionally substituted or unsubstituted aryl, heteroaryl or nitrate ester group, and at least one of $R_1$, $R_2$ and $R_3$ contains a nitrate ester group.

The compounds of formula (I), in a preferred embodiment, have a structure of formula (II):

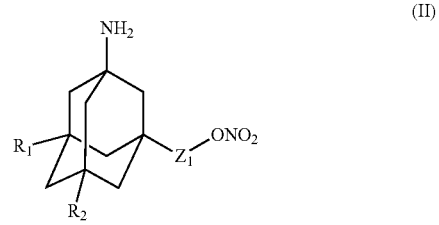

wherein:

$R_1$ and $R_2$ are each independently hydrogen, straight-chain or branched-chain alkyl, optionally substituted or unsubstituted aryl or heteroaryl;

$Z_1$ is a straight- or branched-carbon chain connecting to the nitrate ester group of $R_3$, wherein $Z_1$ can be substituted with heteroatom, alkyl, aryl and heteroaryl, and $Z_1$ can have one to six carbon atoms, for example, 1-6, 1-5, 2-6, 2-5, 2-4 or 3-6.

Of the compounds of formula (II), preferably, at least one of $R_1$ and $R_2$ is hydrogen.

Of the compounds of formula (II), preferably, $R_2$ is hydrogen, $R_1$ is a straight-chain or branched-chain alkyl, and the number of carbon atoms contained in $Z_1$ and $R_3$ together is no less than 3, preferably no less than 4, such as 4-6.

Of the compounds of formula (II), further preferably, $R_1$ and $R_3$ are each a nitrate ester group, and thus the compounds have a structure of formula (III):

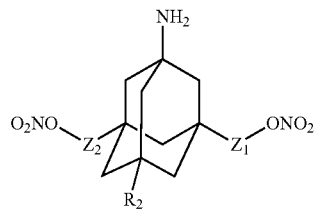

(III)

wherein:

$R_2$ is hydrogen, straight-chain or branched-chain alkyl, optionally substituted or unsubstituted aryl or heteroaryl;

$Z_1$ and $Z_2$ are each independently a straight- or branched-carbon chain connecting to a nitrate ester group, wherein $Z_1$ and $Z_2$ each independently can be substituted with heteroatom, alkyl, aryl and heteroaryl, and $Z_1$ and $Z_2$ each independently can have one to six carbon atoms, for example, 1-6, 1-5, 2-6, 2-5, 2-4 or 3-6.

The compounds of formula (III), preferably, are selected from the group consisting of:

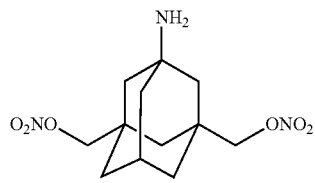
NM-008

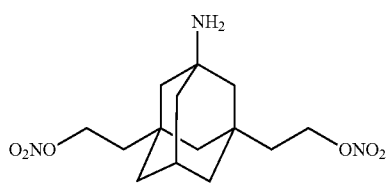
NM-009

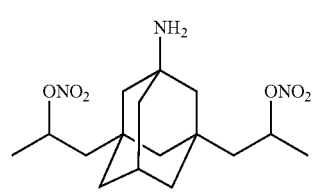
NM-010

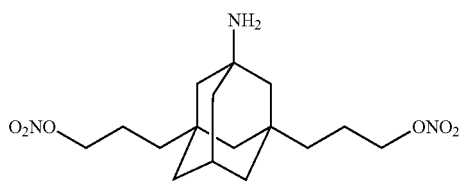
NM-011

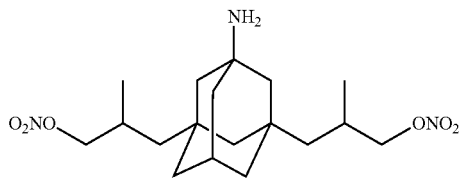
NM-012

Of the compounds of formula (I), further preferably, $R_1$, $R_2$ and $R_3$ are each a nitrate ester group, and thus the compounds have a structure of formula (III):

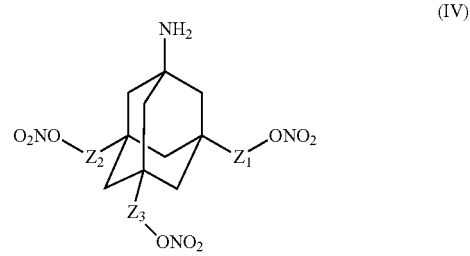

(IV)

wherein:

$Z_1$, $Z_2$ and $Z_3$ are each independently a straight- or branched-carbon chain connecting to the nitrate ester group of $R_1$, $R_2$ and $R_3$ respectively, wherein $Z_1$, $Z_2$ and $Z_3$ each independently can be substituted with heteroatom, alkyl, aryl and heteroaryl, and $Z_1$, $Z_2$ and $Z_3$ independently have have one to six carbon atoms, for example, 1-6, 1-5, 2-6, 2-5, 2-4 or 3-6.

In some preferred embodiments, the compounds of formula (I) include, but not limited, specific structures below:

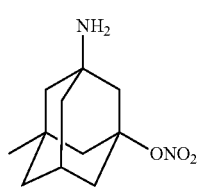
NM-001

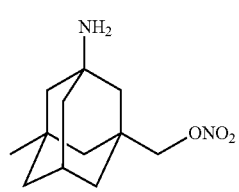
NM-002

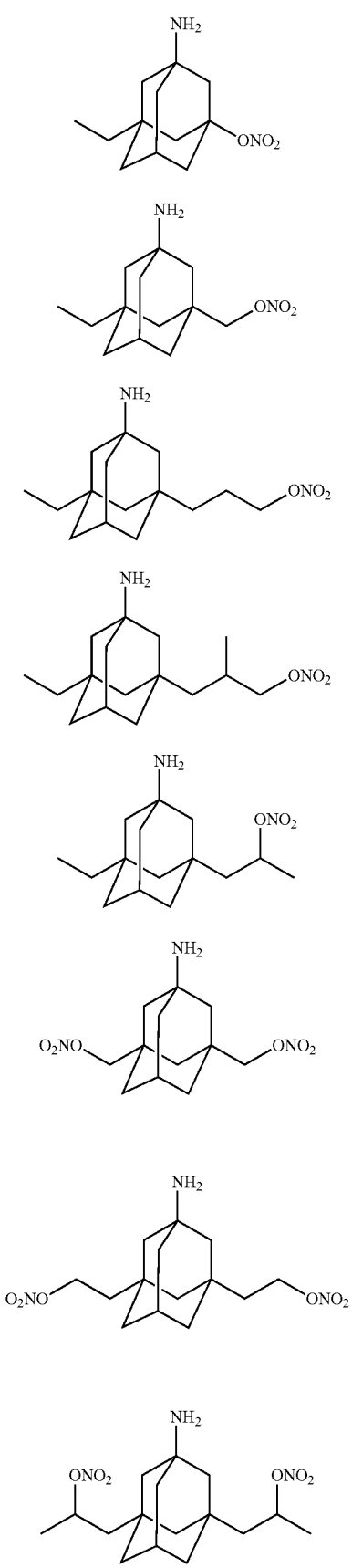

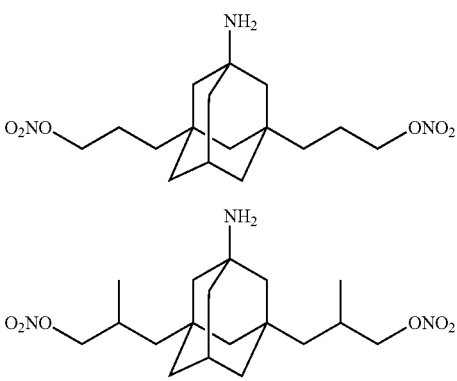

The present invention further provided a method for preparation of amantadine derivatives. The method comprises: using starting materials of adamantine optionally substituted or unsubstituted with bromo, alkyl or alkyl carboxylic group, introducing a amino group via Ritter reaction, and then forming a nitrate ester group on a substituted side chain of the amantadine via esterification of a hydroxy attached on adamantyl ring by using fuming nitric acid.

The compounds of the invention are effective for the protection of cells especially nerve cells, and can be used in manufacture of supplements or medicaments. The medicaments can include a therapeutically effective amount of the compound described herein with the structure of formula (I) or pharmaceutically acceptable salt thereof.

The compounds of the invention showed mechanisms of multiple functions, including the functions of inhibiting NMDA, releasing NO, inhibiting calcium influxes, removing radicals and protection of cells especially nerve cells. Thus, the compounds may be used for preparing cell protecting medicaments for prevention or treatment of diseases related to elevated calcium ions, excessive production of free radicals or excessive activation of NMDA receptors, such as Alzheimer's disease, Parkinson's disease, stroke, Huntington's disease, amyotrophic lateral sclerosis, myasthenia gravis, glaucoma and so on. The methods for prevention or treatment of such diseases comprise administering to a patient the medicaments prepared from the compounds containing an effective amount of the compounds of formula (I) to (V) described herein or pharmaceutically acceptable salt thereof, or a drug complex thereof.

The following definitions are used to describe and define the meaning and scope of the terms used herein.

As used herein, the term "alkyl" refers to unsubstituted or substituted straight, branched or cyclic alkyl chain having up to 10 carbon atoms. Straight-chain alkyl groups include, for example, saturated alkyl groups such as methyl, ethyl, n-propyl, n-butyl, n-pentyl, n-hexyl, n-heptyl and n-octyl, and unsaturated alkyl groups such as those containing ethylenic, acetylenic, carbonyl and cyano groups. Branched-chain alkyl groups include, for example, isopropyl, butyl, isobutyl, tert-butyl and neopentyl. Cyclic alkyl ("cycloalkyl") groups include, for example, cyclopropyl, cyclobutyl, cyclopentyl and cyclohexyl. Alkyl can have one or more hydrophobic substituents. The non-limiting examples of the substituents include $N(CH_3)_2$, F, Cl, Br, I, $OCH_3$, $CO_2CH_3$, CN, aryl and heteroaryl. The term "alkyl" also refers to unsubstituted or substituted straight, branched or cyclic alkyl having up to 10 carbon atoms and at least one heteroatom (e.g., nitrogen, oxygen or sulfur) therein. The straight alkyl includes, for example, $CH_2CH_2OCH_3$, $CH_2CH_2N(CH_3)_2$ and $CH_2CH_2SCH_3$. The branched alkyl includes, for example, $CH_2CH(OCH_3)CH_3$, $CH_2CH(N(CH_3)_2)CH_3$ and $CH_2CH(OCH_3)CH_3$. The cyclic alkyl includes, for example, six-membered rings, such as $CH(CH_2CH_2)_2O$, $CH(CH_2CH_2)_2NCH_3$ and $CH(CH_2CH_2)_2S$, and the corresponding five-membered rings.

The term "aryl" refers to unsubstituted or substituted aromatic, carbocyclic group and heteroaryl. An aryl group can be either monocyclic or fused polycyclic. The aryl can be substituted with one or more substituents, including but not limited to $N(CH_3)_2$, F, Cl, Br, I, $OCH_3$, $CO_2CH_3$, CN, aryl and heteroaryl.

Heteroaryl can be a substituted or unsubstituted monocyclic or polycyclic group having at least one heteroatom, such as nitrogen, oxygen and sulfur. For example, a typical heteroaryl groups containing one or more nitrogen atoms may include, for example, tetrazolyl, pyrrolyl, pyridyl (such as pyrid-4-yl, pyrid-3-yl, pyrid-2-yl), pyridazinyl, indyl, quinolyl (such as quinol-2-yl, quinol-3-yl), imidazolyl, isoquinolyl, pyrazolyl, pyrazinyl, pyrimidinyl, pyridonyl or pyridazinyl; a typical hetroaryl having one oxygen atom includes fur-2-yl, fur-3-yl or benzofuryl; a typical heteroaryl containing one surfer atom may include, for example, thienyl, benzothienyl; a typical heteroaryl group containing an oxygen atom may include, for example, 2-furyl, 3-furyl or benzofuryl; a typical heteroaryl comprising more than one kind of heteroatoms includes furoazetidinyl, oxazolyl, isoxazolyl, thiazolyl and phenothioxinyl. The hetercycle group can be substituted by one or more substituents. Those substituents include O-alkyl, NH-alkyl, N (alkyl)$_2$, NHC(O) alkyl, F, Cl, Br, I, OH, $OCF_3$, $CO_2$— alkyl, CN, and aryl or polyaryl group.

The term "pharmaceutically acceptable" means that a compound has no unacceptable toxicity in a salt or excipient. The pharmaceutically acceptable salts include inorganic anions such as chlorine ion, bromine ion, iodine ion, sulfuric acid radical, sulfurous acid radical, nitric acid radical, nitrous acid radical, phosphoric acid radical, hydrogen phosphoric acid radical and the like. Organic anions include acetic acid radical, pyruvic acid radical, propionic acid radical, cinnamic acid radical, tosylic acid radical, citric acid radical, lactic acid radical, gluconic acid radical and the like. Pharmaceutically acceptable excipients are described below (see also, E. W. Martin, in Remington's Pharmaceutical Sciences Mack Publishing Company (1995), Philadelphia, Pa., 19$^{th}$ ed).

The novel compounds of the present invention comprise those of formulas (I) to (VIII) described above. The compounds also have at least one of the substituents selected from amido, aster and nitrate group on the amantadine structure, and thus those compounds have multifunctional mechanisms to inhibit the monoamine oxidase and cholinesterase, release NO, release $H_2S$ and scavenge free radicals, and have a good protective effect to cells, especially the nerve cells. The compounds can be used in preparation of medicaments with protective effect of cells, and can be used for the prevention and treatment of the diseases related to monoamine oxidase, cholinesterase or free radicals, while such diseases are generally referred to those related to neurodegeneration and free radicals and the like. Such diseases include, but not limited to, the diseases related to monoamine oxidase, such as Parkinson's disease, Alzheimer's disease, dementia, hypertension, diarrhea, depression, asthma and allergies; the diseases related to cholinesterase, such as Alzheimer's disease, Parkinson's disease, Huntington's disease, amyotrophic lateral sclerosis, myasthenia gravis, glaucoma, hyperthyroidism, hypertension, bronchial asthma, IV hyperlipoproteinemia type renal and kidney failure; the diseases related to NO or oxidative stress damage or free radicals, such as stroke, brain trauma, epilepsy, Parkinson's disease, Huntington's disease, amyotrophic lateral sclerosis, Alzheimer's disease, hypoxic-ischemic brain damage, cerebral hemorrhage, dementia, ischemic heart disease, blood clots, atherosclerosis, hypercholesterolemia, emphysema, cataracts, diabetes, acute pancreatitis, alcohol-induced liver disease, kidney damage and cancer; the diseases related to $H_2S$, such as cardiovascular disease, inflammation, atherosclerosis, diabetes, Alzheimer's disease, Parkinson's disease, obesity, cancer, stroke, and traumatic brain damage; and also the diseases related to neurodegeneration such as cerebral ischemia, Parkinson's disease, Alzheimer's disease, amyotrophic lateral sclerosis, ataxia telangiectasia, bovine spongiform encephalopathy, Creutzfeldt-Jakob disease, spinocerebellar ataxia, multiple sclerosis, primary lateral sclerosis, and spinal muscular atrophy.

The present invention provided compounds having an ester group (includes an optionally substituted or unsubstituted carbamate group), amino and/or nitrate ester group, and derivatives thereof, and the compounds can be administered to patients in the form of a pharmaceutically acceptable salt or a pharmaceutical complex. Certain complex may need to form a pharmaceutical composition with a suitable carrier or excipient. The term "therapeutically effective amount" refers to an amount of the compounds that is necessary to achieve a desired effect.

A variety of preparations can be used to formulate pharmaceutical compositions containing the compounds with multiple functions of mechanisms, including solid, semi solid, liquid and gaseous forms (Remington's Pharmaceutical Sciences, Mack Publishing Company (1995), Philadelphia, Pa., 19$^{th}$ ed). Tablets, pills, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

When the compounds and derivatives described herein are given via injection, they can be formulated by dissolving, suspending or emulsifying it in an aqueous or nonaqueous solvent. Vegetable or similar oils, synthetic aliphatic acid glycerides, esters of higher aliphatic acids and propylene glycol are examples of nonaqueous solvents. The compound is preferably formulated in aqueous solutions such as Hank's solution, Ringer's solution or physiological saline buffer.

When the compounds and derivatives described herein are given orally, they can be formulated through combination with pharmaceutically acceptable carriers that are known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethyl-cellulose, sodium carboxymethylcellulose and polyvinylpyrrolidone (PVP).

The compounds described herein are can also be delivered in an aerosol spray preparation from a pressurized pack and a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions according to the present invention contain a therapeutically effective amount of the compounds of multiple mechanisms. The amount of the compound will depend on the patient being treated. The patient's weight, severity of illness, manner of administration and judgment of the prescribing physician should be taken into account in deciding the proper amount. The determination of a therapeutically effective amount of the compounds described herein should be made by an experienced physician.

Although a therapeutically effective amount of the compound described herein or its derivative will vary according to the patient being treated, suitable doses will typically be in the range between about 10 mg and 10 g of the compound.

The present invention has the advantages over the prior art: the present invention provides substances with novel structures and multiple mechanisms or functions, and such substances can be used for inhibiting NMDA, releasing NO, inhibiting calcium influxes, removing radicals and protection of cells especially nerve cells. Thus, the compounds may be used for preparing cell protecting medicaments for prevention or treatment of diseases, which usually include: neuro-degeneration related diseases such as Alzheimer's disease and Parkinson's disease, and free radical related diseases such as stroke and heart disease.

BRIEF DESCRIPTION OF THE DRAWINGS

FIG. 3 is a scheme of exemplary Synthesis of compound NM-005.

FIG. 4 is a scheme of exemplary Synthesis of compound NM-008.

FIG. 5 is a scheme of exemplary Synthesis of compound NM-009.

FIG. 6 is a scheme of exemplary Synthesis of compound NM-011.

DETAILED DESCRIPTION OF THE EMBODIMENTS

Figure 1:
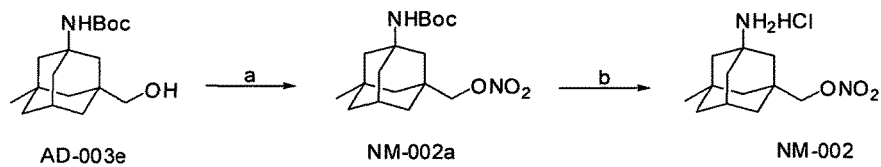
FIG. 1 is a scheme of exemplary Synthesis of compound NM-002.
Figure 2:
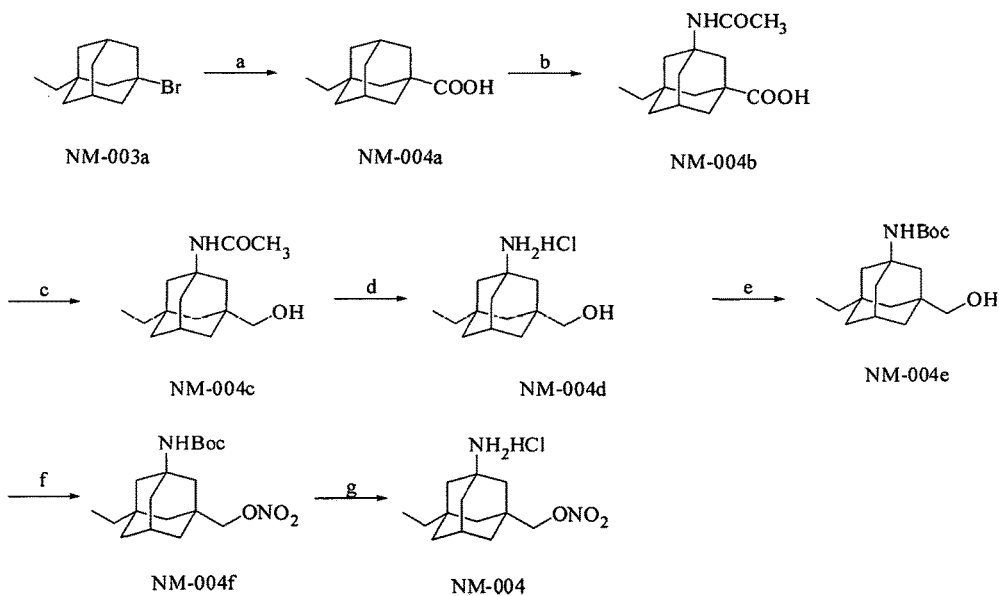
FIG. 2 is a scheme of exemplary Synthesis of compound NM-004.
Figure 7:
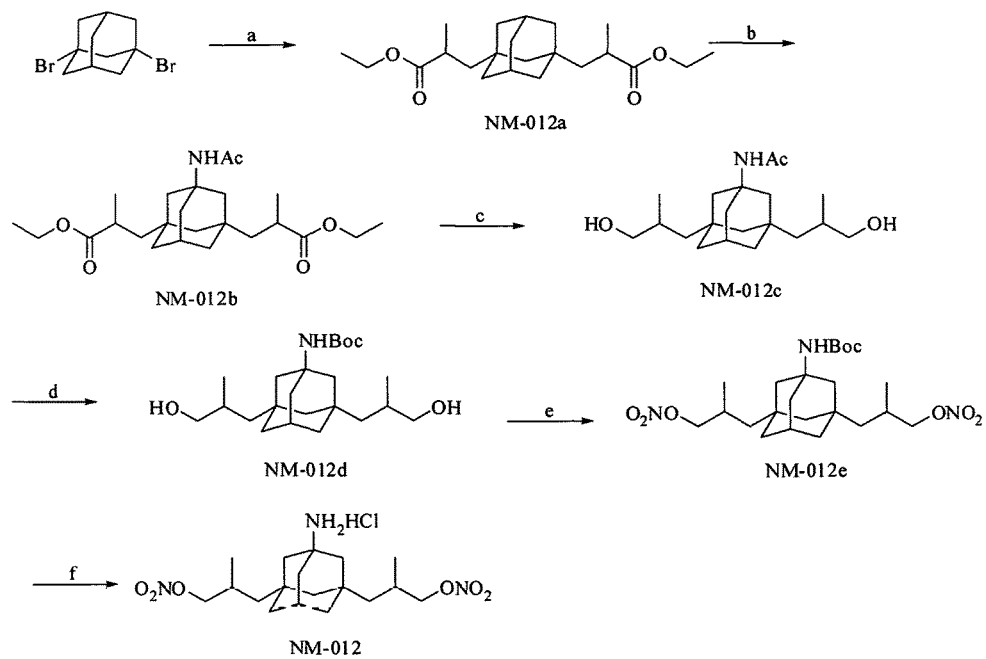
FIG. 7 is a scheme of exemplary Synthesis of compound NM-012.

The following examples are intended for illustration only and are not intended to restrict the scope of the present invention in any way.

Example 1. Synthesis of Compound NM-002a

Compound AD-003e (1.48 g, 5 mmol) was dissolved in 30 mL of dry methylene chloride and cooled with an ice-water bath. A mixed solution (3 mL) of acetic anhydride and fuming nitric acid (3:2 by volume) was added. The reaction continued for 10-15 minutes with an ice-water bath. The reaction mixture was poured into 30 mL of 1N sodium bicarbonate solution, and then methylene chloride was separated, and the aqueous layer was extracted with dichloromethane (20 mL×3). The organic layers were combined, washed with water (30 mL), dried over anhydrous sodium sulfate, and the filtered. The dichloromethane layer was distilled under reduced pressure to obtain a crude product as colorless oil, which was separated by silica column chromatography (petroleum ether:dichloromethane=10:1) to give NM-002a as a colorless oil (1.07 g, 62.9%). ESI-MS: m/z 340.2 ([M]$^+$). $^1$H-NMR (DMSO-d6, ppm): 0.83 (s, 3H), 1.15-1.24 (m, 2H), 1.26-1.47 (m, 14H), 1.56-1.80 (m, 5H), 2.06-2.14 (m, 1H), 4.22 (s, 2H), 6.51 (s, 1H).

Example 2. Synthesis of Compound NM-002

To compound NM-002a (680 mg, 2 mmol) was added a saturated solution of hydrogen chloride in ether (5 mL). The reaction was run at room temperature, and monitored with TLC. When the reaction was completed, a white solid was precipitated. The resulting mixture was filtered, and a white solid was obtained and washed with dry ether to give pure NM-002 (390 mg, 70.7%). ESI-MS: m/z 341.0 ([M+H]$^+$). $^1$H-NMR (DMSO-d6, ppm): 0.88 (s, 3H), 1.19-1.29 (m, 2H), 1.30-1.38 (m, 2H), 1.38-1.52 (m, 4H), 1.54-1.64 (m, 2H), 1.66-1.73 (m, 2H), 2.18-2.24 (m, 1H), 4.29 (s, 2H), 8.11 (s, 3H).

Example 3. Synthesis of Compound NM-004a

In a 50 mL round-bottom flask placed in an ice water bath was added 20 mL of concentrated sulfuric acid, 2 mL of n-hexane and 970 mg of compound NM-003a (4 mmol). Being kept with the ice-water bath, formic acid (1.8 mL) was slowly added dropwise, and then the reaction was run for 3 hours with the ice-water bath. The reaction mixture was poured into 100 mL of ice water, and a solid was precipitated. The resulting mixture was allowed to stand and then was filtered under vacuum to give a pale yellow solid. The solid was dried, dissolved in ethyl acetate, and basified to about pH 9-10 with an aqueous solution of sodium hydroxide. Aqueous layer was separated, and the organic layer was extracted with aqueous solution of sodium hydroxide (30 mL×3). The aqueous layers were combined, and then acidified with a solution of dilute hydrochloric acid to about pH 3. The resulting materials were filtered under vacuum, and dried to give a pure compound NM-004a (640 mg, 77%). ESI-MS: m/z 207 ([M−H]$^-$). $^1$H-NMR (DMSO-d6, ppm): 0.76 (t, 3H, J=7.5 Hz), 1.11 (q, 2H, J=7.5 Hz), 1.31-1.44 (m, 4H), 1.47 (s, 2H), 1.51-1.64 (m, 2H), 1.66-1.81 (m, 4H), 2.01 (m, 2H), 11.99 (s, 1H).

Example 4. Synthesis of Compound NM-004b

In a 50 mL round-bottom flask was placed 624 mg of compound NM-004a (3 mmol), which was cooled with an ice water bath. A concentrated nitric acid (0.55 mL) was added with stirring. To the mixture, a concentrated sulfuric acid (1.3.5 mL) was added dropwise, and the reaction was kept in an ice bath for 1 hour. Acetonitrile (2.5 mL, 4.8 mmol) was added dropwise, and the reaction was kept with an ice bath for 1 hour. The reaction mixture was poured into 20 mL of ice water, stirred vigorously for 30 minutes, and allowed to stand overnight. A white solid was precipitated.

The resulting mixture was filtered under vacuum, and the solid was washed with suitable amount of water and dried to give the compound NM-004b (580 g, 73%) to be used directly in the next reaction step without further purification. ESI-MS: m/z 266 ([M+H]$^+$). $^1$H-NMR (DMSO-d6, ppm): 0.74 (t, 3H, J=7.5 Hz), 1.15 (q, 2H, J=7.5 Hz), 1.26-1.35 (m, 2H), 1.36-1.47 (m, 2H), 1.52-1.70 (m, 4H), 1.72-1.86 (m, 5H), 1.88-1.98 (m, 2H), 2.13 (m, 1H), 7.43 (s, 1H).

Example 5. Synthesis of Compound NM-004c

A compound NM-004b (878 mg, 3.3 mmol) was dissolved in 10 mL of dried tetrahydrofuran, being cooled with an ice water bath. To the mixture was added sequentially 0.5 mL of triethylamine and 0.5 mL of ethyl chloroformate. After 30 minutes, the ice bath was removed. The reaction was run for 4 hours at room temperature. The resulting materials were filtered, and the residue was washed with an appropriate amount of tetrahydrofuran. The filtrate was collected, to which was added 1.5 g of sodium borohydride. Then 1 mL of water was added dropwise with dropping funnel within 1 hour. Then, the reaction continued at room temperature for 1 hour and monitored with TLC. After the reaction being completed, 30 mL of water was added, and tetrahydrofuran was evaporated to dryness in a rotavap under reduced pressure. The aqueous layer was extracted with ethyl acetate (20 mL×4). The organic layers were combined, and washed with 0.5 N hydrochloric acid (25 mL), and saturated aqueous solution of sodium chloride and water, and dried over anhydrous sodium sulfate. The resulting solution was evaporated under reduced pressure to obtain a crude product as an oil, which was separated by silica column chromatography (petroleum ether:ethyl acetate=1:1) to give NM-004c as a white solid (348 mg, 42%). ESI-MS: m/z 252.2 ([M+H]$^+$). $^1$H-NMR (DMSO-d6, ppm): 0.76 (t, 3H, J=7.5 Hz), 1.03-1.20 (m, 4H), 1.28 (m, 4H), 1.58 (m, 4H), 1.75 (m, 5H), 2.09 (s, 1H), 3.02 (d, 2H, J=5.5 Hz), 4.38 (t, 1H, J=5.5 Hz), 7.33 (s, 1H).

Example 6. Synthesis of Compound NM-004d

In a 250 mL round-bottom flask were added compound NM-004c (1.26 g, 5 mmol), solid of sodium hydroxide (3 g) and diethylene glycol (20 mL). The reaction mixture was refluxed at 170° C. for 15 hours, and then cooled to room temperature. The resulting materials were poured into 40 g of crushed ice. After stirring evenly, the mixture was extracted with ethyl acetate (20 mL×4). The organic layers were combined, and washed with 30 mL of water and 30 mL of saturated solution of sodium chloride, and dried with anhydrous sodium sulfate. The solvent was evaporated to give crude product as a pale yellow oil. The crude product was dissolved in 50 mL of dry ethyl acetate, introduced with dry HCl with stirring, and a large amount of white solid was precipitated. After filtered under vacuum, the solid was washed with appropriate amount of dry ethyl acetate to give NM-004d as a white solid (850 mg, 69.4%). ESI-MS: m/z 210.3 ([M+H]$^+$). $^1$H-NMR (DMSO-d6, ppm): 0.74 (t, 3H, J=7.6 Hz), 1.15 (q, 2H, J=7.6 Hz), 1.26-1.35 (m, 2H), 1.36-1.47 (m, 2H), 1.53-1.68 (m, 4H), 1.74-1.85 (m, 3H), 1.88-1.96 (m, 2H), 2.13 (m, 1H), 7.43 (s, 3H).

Example 7. Synthesis of Compound NM-004e

A compound NM-004d (2.45 g, 10 mmol) was dissolved in 20 mL of water, basified to about pH 10 with a solution of sodium hydroxide, and extracted with ethyl acetate (30 mL×4). The organic layers were combined, washed with 30 mL of water, and dried with anhydrous sodium sulfate. The solvent was removed under reduced pressure to give free amine as a colorless oil (1.57 g, 7.5 mmol). Without further purification, the oil was dissolved in 50 mL of dry tetrahydrofuran, and were added in order with 1.56 g of triethylamine (15.6 mmol), 2.55 g of Boc anhydride (11.7 mmol) and 10 mg of DMAP. The reaction was run for 5 hours at room temperature and monitored with TLC. After the reaction being completed, 30 mL of saturated ammonium chloride solution was added to quench the reaction. The solvent was evaporated to dryness under reduced pressure, and the residue was extracted with ethyl acetate (50 mL×4). The organic layers were combined and washed with 30 mL of 0.1 N hydrochloric acid and 30 mL of saturated aqueous sodium chloride solution, and dried with anhydrous sodium sulfate. The solvent was evaporated to dryness under reduced pressure to give a crude product as a colorless oil, which was separated by silica column chromatography (petroleum ether:ethyl acetate=1:1) to give NM-004e as a white solid (1.58 g, 68%). ESI-MS: m/z 310.3 ([M+H]$^+$). $^1$H-NMR (DMSO-d6, ppm): 0.75 (t, 3H, J=7.5 Hz), 1.03-1.19 (m, 4H), 1.24 (m, 4H), 1.36 (s, 9H), 1.44-1.58 (m, 4H), 1.52-1.73 (m, 2H), 2.08 (s, 1H), 3.02 (d, 2H, J=5.5 Hz), 4.38 (t, 1H, J=5.5 Hz), 6.36 (s, 1H).

Example 8. Synthesis of Compound NM-004f

Compound NM-004e (620 mg, 2 mmol) was dissolved in 10 mL of dry methylene chloride, and cooled with an ice-water bath. A mixed solution (2 mL) of acetic anhydride and fuming nitric acid (in a ratio of 3:2 by volume) was added. The reaction was run with an ice-water bath for 10-15 minutes. The reaction solution was added to 10 mL of 1 N sodium bicarbonate solution, and the dichloromethane was separated, and the aqueous layer was extracted with dichloromethane (10 mL×3). The organic layers were combined, washed with 10 mL of water, dried with anhydrous sodium sulfate, and filtered. The solvent was distilled under reduced pressure to give crude product as a colorless oil, which was separated by silica column chromatography (petroleum ether:dichloromethane=10:1) to give NM-004f as a colorless (505 mg, 73.4%). ESI-MS: m/z 377.2 ([M+Na]$^+$). $^1$H-NMR (DMSO-d6, ppm): 0.76 (t, 3H, J=7.5 Hz), 1.08-1.23 (m, 4H), 1.26-1.49 (m, 14H), 1.56-1.82 (m, 5H), 2.12 (m, 1H), 4.23 (s, 2H), 6.50 (s, 1H).

Example 9. Synthesis of Compound NM-004

To compound NM-004f (710 mg, 2 mmol) was added 5 mL of hydrogen chloride saturated ether solution, and the reaction was run at room temperature. When the reaction was completed, a white solid was precipitated. The resulting materials were filtered and a white solid was obtained and washed with anhydrous ether to give pure NM-004, which was then dried to give NM-004 (380 mg, 65.5%). ESI-MS: m/z 255.1 ([M+H]$^+$). $^1$H-NMR (DMSO-d6, ppm): 0.78 (t, 3H, J=7.5 Hz), 1.15-1.28 (m, 4H), 1.30-1.39 (m, 2H), 1.40-1.55 (m, 4H), 1.57-1.67 (m, 2H), 1.71 (s, 2H), 2.23 (m, 1H), 4.30 (s, 2H), 8.21 (s, 3H).

Example 10. Synthesis of Compound NM-005a

Compound NM-003a (3.66 g, 15.0 mmol) was dissolved in 45 mL of dry toluene, and 0.122 g of AIBN (0.74 mol), 4.95 g of n-Bu3SnH (16.7 mmol), and 3.10 g of ethyl acrylate (31.0 mmol) were added in order. The reaction was refluxed at 110° C. under nitrogen for 3 hours and monitored with TLC. After the reaction being completed, the reaction mixture was cooled and was poured into 105 mL of 0.2 M aqueous ammonia, stirred for 1 hour, and extracted with ethyl acetate (100 mL×4). The organic layers were combined and dried with anhydrous sodium sulfate. The resulting materials were filtered, and the solvent was removed under reduced pressure to give a colorless transparent liquid, which was separated by silica column chromatography (petroleum ether:ethyl acetate=6:1) to give NM-005a as a colorless transparent liquid (2.50 g, 62.8%). $^1$H-NMR (DMSO-$d_6$, ppm): 0.72 (t, 3H, J=7.5 Hz), 1.10 (m, 4H), 1.17 (t, 3H, J=7.8 Hz), 1.32 (m, 10H), 1.53 (s, 2H), 1.97 (s, 2H), 2.21 (t, 2H, J=8.1 Hz), 4.02 (q, 1H, J=7.2 Hz).

Example 11. Synthesis of Compound NM-005b

To the compound NM-005a (2.50 g, 9.5 mmol) were added 60 mL of methanol and 5 mL of water. The mixture was stirred to be dissolved, and 3.2 g of potassium hydroxide (57 mmol) was added. The reaction was run at room temperature for 12 hours and monitored with TLC. After the reaction being completed, the solvent was removed under reduced pressure. To the residue was added 30 mL of water, and was extracted with 20 mL of ethyl acetate to remove organic impurities. The aqueous layer was adjusted to pH 1-2 with concentrated hydrochloric acid, and then a large amount of white solid was precipitated. The resulting materials were filtered under vacuum, and the filter cake was washed with small amount of water, and dried to give NM-005b as a white solid (1.60 g, 71.6%). ESI-MS: m/z 237.1 ([M+H]$^+$). $^1$H-NMR (DMSO-$d_6$, ppm): 0.75 (t, 3H, J=7.5 Hz), 1.10 (m, 4H), 1.32 (m, 10H), 1.54 (s, 2H), 1.97 (s, 2H), 2.14 (t, 2H, J=8.1 Hz), 11.98 (s, 1H).

Example 12. Synthesis of Compound NM-005c

Compound NM-005b (1.6 g, 6.8 mmol) was placed in a 50 mL round-bottom flask, and cooled with an ice bath. Concentrated nitric acid (1.1 mL) was added with stirring. To the mixture was added dropwise 6.8 mL of concentrated sulfuric acid, then reacted for 1 hour with an ice bath. To the reaction was slowly added dropwise 5 mL of acetonitrile, and run in an ice bath for 1 hour. The reaction solution was poured into 30 mL of ice water, and stirred vigorously for 30 minutes. The resulting materials were extracted with ethyl acetate (50 mL×5), and the organic layers were combined, dried with anhydrous sodium sulfate, and filtered. The solvent was removed under reduced pressure to give a colorless viscous liquid, which was separated by silica column chromatography (ethyl acetate as eluent) to give NM-005c as a colorless transparent viscous semi-solid (1.60 g, 80.6%). $^1$H-NMR (DMSO-$d_6$, ppm): 0.75 (t, 3H, J=7.5 Hz), 1.11 (m, 4H), 1.28 (m, 6H), 1.54 (m, 4H), 1.73 (m, 5H), 2.08 (s, 1H), 2.16 (m, 2H), 3.16 (s, 1H), 1.77 (m, 1H), 4.38 (m, 2H), 4.40 (s, 1H).

Example 13. Synthesis of Compound NM-005d

Compound NM-005c (2.8 g, 9.5 mmol) was dissolved in 10 mL of dry tetrahydrofuran with cooling in an ice bath. Then 1.5 mL of triethylamine and 1.5 mL of ethyl chloroformate (15.8 mmol) were added in order, and, after 30 minutes the ice bath was removed. The reaction was run at room temperature for 4 hours and filtered, and the filter cake was washed with tetrahydrofuran. The filtrate was collected, and 2.7 g of sodium borohydride (0.07 mol) was added and then 1.8 mL of water was added dropwise. The reaction was run at room temperature for 2 hours, and then 50 mL of water was added. The solvent was removed under reduced pressure. The aqueous layer was extracted with ethyl acetate (50 mL×5), and the organic layers were combined, washed with a saturated aqueous solution of sodium chloride, and dried with anhydrous sodium sulfate. The resulting mixture was filtered, and the solvent was removed under reduced pressure to give a crude product as an oil, which was then separated by silica column chromatography (methanol:ethyl acetate=1:6) to give NM-005d as a colorless transparent viscous semi-solid (1.7 g, 63.75%). ESI-MS: m/z 280.1 ([M+H]$^+$). $^1$H-NMR (DMSO-$d_6$, ppm): 0.75 (t, 3H, J=7.5 Hz), 1.11 (m, 4H), 1.36 (m, 6H), 1.54 (m, 4H), 1.73 (m, 5H), 2.08 (s, 1H), 2.18 (m, 2H), 3.57 (m, 2H).

Example 14. Synthesis of Compound NM-005e

To a 100 mL round-bottom flask were added in order the compound NM-005d (1.7 g, 6.1 mmol), sodium hydroxide (5.5 g, 0.14 mol) and diethylene glycol (35 mL). The mixture was refluxed at 175° C. for 16 h, and then cooled to room temperature. The resulting materials were poured into 50 g of crushed ice with stirring, and extracted with ethyl acetate and methyl tert-butyl ether (4:1 by volume, 50 mL×6). The organic phases were combined, and washed with saturated sodium chloride solution, and dried with anhydrous sodium sulfate. The resulting materials were filtered, and the solvent was removed under reduced pressure to give 1.1 g of brown liquid, to which, without further purification, a redistilled dry dichloromethane (50 mL) was added directly, and then 2.5 mL of triethylamine and 1.1 g of Boc anhydride (5 mmol) were added in order. The reaction was stirred at room temperature for 5 hours, and monitored with TLC. After the reaction being completed, the reaction solution was washed several times with a saturated sodium chloride solution. The organic phase was dried with anhydrous sodium sulfate. The resulting materials were filtered, and the solvent was removed under reduced pressure to give a brown oil, which was separated by silica column chromatography (petroleum ether:ethyl acetate=1:5) to give NM-005e as a colorless liquid (0.48 g, 23.38%). $^1$H-NMR (CDCl$_3$-d, ppm): 0.80 (t, 3H, J=7.5 Hz), 1.14 (m, 2H), 1.20 (m, 4H), 1.33 (m, 6H), 1.43 (s, 9H), 1.51 (m, 2H), 1.61 (m, 2H), 1.72 (m, 1H), 1.78 (m, 2H), 2.17 (m, 1H), 3.61 (m, 2H, J=6.3 Hz), 4.43 (s, 1H).

Example 15. Synthesis of Compound NM-005f

Compound NM-005e (380 mg, 1.1 mmol) was dissolved in 8 mL of dry methylene chloride, and cooled with an ice bath. Then 1.2 mL of a mixed solution of acetic anhydride and fuming nitric acid (in a ratio of 3:2 by volume) was added. The reaction was run for 10-15 minutes, and monitored with TLC. After the reaction being completed, the reaction solution was poured into 40 mL of 1 N sodium bicarbonate solution, and extracted with dichloromethane continued (20 mL×3). The organic layers were combined, and washed with a solution of saturated sodium chloride, and dried with anhydrous sodium sulfate. The resulting materials were filtered, the solvent removed under reduced pressure to give a colorless oil, which was separated by silica column chromatography (petroleum ether:ethyl acetate=20:1) to give NM-005f as a colorless oil (230 m, 53.41%). $^1$H-NMR (CDCl$_3$-d, ppm): 0.76 (t, 3H, J=7.5 Hz), 1.10 (m, 2H), 1.23 (m, 6H), 1.33 (m, 2H), 1.40 (s, 9H), 1.51 (m, 2H), 1.68 (m, 4H), 1.68 (m, 4H), 1.77 (m, 1H), 4.38 (m, 2H), 4.40 (s, 1H).

Example 16. Synthesis of Compound NM-005

Compound NM-005f (110 mg, 0.29 mmol) was placed in a 25 mL round-bottom flask, and 10 mL of saturated hydrogen chloride solution was added. The reaction was run at room temperature for 30-45 minutes, and monitored with TLC. After the reaction being completed, the solvent was removed under reduced pressure to give a colorless oil. Then 20 mL of anhydrous ether was added and the solvent was removed under reduced pressure, which was repeated several times, until a solid was precipitated. The resulting materials were filtered, and the filter cake was washed with a small amount of anhydrous diethyl ether, and dried to give NM-005 as a white solid (32 mg, 39.4%). ESI-MS: m/z 283.1 ([M+H]$^+$). $^1$H-NMR (DMSO-d$_6$, ppm): 0.77 (t, 3H, J=7.5 Hz). 1.18 (m, 6H), 1.30 (m, 4H), 1.46 (m, 4H), 1.60 (m, 2H), 1.67 (m, 2H), 2.18 (m, 1H), 4.49 (t, 2H, J=6.6 Hz), 8.18 (s, 3H).

Example 17. Synthesis of Compound NM-008a

In a two-necked round-bottom flask with a condenser was added 1,3-adamantanediol (8.4 g, 50 mmol), which cooled with an ice bath. Then 56 mL of concentrated sulfuric acid was added with stirring, and 5 mL of anhydrous acid was slowly added dropwise. After the addition, the mixture was maintained with an ice bath for 2 hours. The reaction was run at room temperature for 10 hours. The pale yellow viscous transparent reaction solution was slowly poured into 200 g of ice water, and then a large amount of white solid was precipitated. The resulting materials were filtered, and the filter cake was washed with water, and then dried to give compound NM-008a (8.9 g, 79.5%). ESI-MS: m/z 223.2 ([M−H]$^−$). $^1$H-NMR (DMSO-d6, ppm): 1.56-1.88 (m, 12H), 2.06 (s, 2H), 12.12 (s, 2H).

Example 18. Synthesis of Compound NM-008b

Compound NM-008a (2.24 g, 10 mmol) was dissolved in 100 mL of dry tetrahydrofuran, and cooled with an ice bath. Then 3.0 mL of triethylamine and 3.0 mL of ethyl chloroformate were added in order. The ice bath was removed 30 minutes later, and the reaction was run at room temperature for 4 hours. The resulting materials were filtered, and the filter cake was washed with tetrahydrofuran. The filtrate was collected, and to which 6 g of sodium borohydride was added, and 3 mL of water was slowly added with dropping funnel within 1 hour. After the water being added completely, the reaction was reacted at room temperature for 1 hour and monitored with TLC. When the reaction was completed, 50 mL of water was added, and organic phase was removed to dryness under reduced pressure. The aqueous layers was extracted with ethyl acetate (40 mL×4). The organic layers were combined, and were washed with 50 mL of 0.5 N hydrochloric acid and saturated sodium chloride aqueous solution and water, respectively, and then dried with anhydrous sodium sulfate. The solvent was evaporated under reduced pressure, to give a crude product as a white solid, which was washed with ethyl acetate to give NM-008b as a white solid (1.08 g, 55%). ESI-MS: m/z 274.2 ([M+2K]$^{2+}$). $^1$H-NMR (DMSO-d6, ppm): 1.14 (s, 2H), 1.26-1.47 (m, 8H), 1.54 (s, 2H), 1.99 (m, 2H), 2.99 (d, 4H, J=5.5 Hz), 4.30 (t, 1H, J=5.5 Hz).

Example 19. Synthesis of Compound NM-008c

In a 25 mL round-bottom flask was placed with a white solid of compound NM-008b (784 mg, 4 mmol), then 5 mL of acetic anhydride was added with stirring. To the suspension was added 2-3 drops (catalytic amount) of perchloric acid. The reaction was run at room temperature for 3 hours. The reaction solution was poured into 20 g of ice water, and extracted with ethyl acetate (20 mL×3). The organic layers were combined and washed with 30 mL of 1 N sodium bicarbonate solution and 30 mL of water, and was dried with anhydrous sodium sulfate. The solvent was evaporated under reduced pressure to obtain a rude product as colorless oil. The crude product was separated by silica column chromatography (petroleum ether:ethyl acetate=10:1) to obtain NM-008c as a colorless oil (1.0 g, 90%). ESI-MS: m/z 298.3 ([M+H$_2$O]$^+$). $^1$H-NMR (DMSO-d6, ppm): 1.284 (s, 2H), 1.36-1.52 (m, 8H), 1.59 (s, 2H), 2.02 (s, 8H), 3.66 (s, 4H).

Example 20. Synthesis of Compound NM-008d

Compound NM-008c (840 mg, 3 mmol) was placed in a 25 mL round-bottom flask, and was cooled with an ice bath. Then 0.55 mL of concentrated nitric acid was added with stirring. To the mixture was slowly added 3.5 mL of concentrated sulfuric acid. The reaction was then run with an ice bath for 1 hour. Acetonitrile (2.5 mL, 4.8 mmol) was slowly added dropwise, the reaction was continued with an ice bath reaction for 1 hour. The reaction mixture was poured into 20 mL of ice water, and the aqueous layer was extracted with ethyl acetate. (20 mL×4). The organic layers were combined, and washed with 30 mL of 1 N sodium bicarbonate solution and 30 mL of water, and was dried with anhydrous sodium sulfate. The solvent was evaporated under reduced pressure to dryness to give a crude product as a colorless oil. The crude product was separated by silica column chromatography (petroleum ether:ethyl acetate=1:3) to obtain compound NM-008d as an oil (425 mg, 42%). ESI-MS: m/z 360.3 ([M+Na]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 21. Synthesis of Compound NM-008e

Compound NM-008d (670 mg, 2 mmol) was placed in a 25 mL round-bottom flask, and 10 mL of 18% HCl was added. The reaction was refluxed for 48 hours. Water was evaporated to dryness under reduced pressure to give a white solid, which was wished with ethyl acetate to obtain NM-008e (296 mg, 60%). ESI-MS: m/z 21.3 ([M+H]$^+$). $^1$H-NMR (DMSO-d6, ppm).

Example 22. Synthesis of Compound NM-008f

Compound NM-008e (500 mg, 2 mmol) was placed in a 25 mL round-bottom flask, and 5 mL of DMF was added. Then triethylamine (800 mg, 8 mmol), Boc anhydride (650 mg, 3 mmol) and DMAP (2 mg) were added in order. The reaction was run at room temperature with stirring for 5 hours and monitored with TLC. After the reaction being completed, 20 mL of saturated ammonium chloride solution was added to quench the reaction. The solvent was evaporated to dryness under reduced pressure, and the aqueous layer was extracted with ethyl acetate (10 mL×4). Organic layers were combined, washed with 10 mL of 0.1 N hydrochloric acid and 10 mL of saturated aqueous sodium chloride solution, and dried with anhydrous sodium sulfate. The solvent was evaporated under reduced pressure to give a crude product as a colorless oil. The crude product was separated by silica column chromatography (petroleum ether:ethyl acetate=1:1) to obtain NM-008f as a white solid (404 mg, 65%). ESI-MS: m/z 312.3 ([M+H]$^+$). $^1$H-NMR (DMSO-d6, ppm): 1.07 (m, 2H), 1.20-1.29 (m, 4H), 1.39 (s, 9H), 1.43-1.59 (m, 4H), 1.62-1.72 (m, 2H), 2.08 (m, 1H), 3.02 (d, 4H, J=5.5 Hz), 4.38 (t, 2H, J=5.5 Hz), 6.39 (s, 1H).

Example 23. Synthesis of Compound NM-008 g

Compound NM-008f (624 mg, 2 mmol) was dissolved in 10 mL of anhydrous dichloromethane, and cooled with an ice bath. Then, 2 mL of mixture solution of acetic anhydride and fuming nitric acid in a ratio 3:2 by volume was added. The reaction was run for 10-15 minutes with an ice bath. The reaction solution was poured into 10 mL of 1 N sodium bicarbonate solution. The solvent phase was separated, and the aqueous phase was extracted with dichloromethane (10 mL×3). Organic layers were combined and washed with 10 mL of water and dried with anhydrous sodium sulfate. After filtration, the filtrate was distilled under reduced pressure to obtain a crude product as a colorless oil, which was separated by silica column chromatography (petroleum ether:dichloromethane=10:1) to give NM-008 g as a colorless oil (600 mg, 75%). ESI-MS: m/z 419.3 ([M+H]$^+$). $^1$H-NMR (DMSO-d6, ppm): 1.37 (s, 9H), 1.40 (m, 6H), 1.60 (m, 2H), 1.72-1.82 (m, 4H), 2.17 (m, 1H), 4.23 (s, 4H), 6.66 (s, 1H).

Example 24. Synthesis of Compound NM-008

To the compound NM-008 g (401 mg, 1 mmol) was added 5 mL solution of saturated hydrogen chloride in ether. The reaction was at room temperature and monitored with TLC. After the reaction being completed, a white solid was precipitated. After being filtered, the white solid was washed with anhydrous ether to give a pure product, which was dried to give NM-008 (380 mg, 65.5%). ESI-MS: m/z 255.1 ([M+H]$^+$). $^1$H-NMR (DMSO-d6, ppm): 1.38-1.54 (m, 6H), 1.60-1.77 (m, 6H), 2.27 (m, 1H), 4.32 (s, 4H), 8.27 (s, 3H).

Example 25. Synthesis of Compound NM-009a

To 100 mL of tetrahydrofuran was added anhydrous 1,3-adamantane diacetic acid (2.52 g, 10 mmol) cooled with an ice bath. To the suspension were added triethylamine (3.0 mL) and ethyl chloroformate (3.0 mL) in order with an ice bath which was maintained for 30 minutes. Then the ice bath was removed, and the reaction was reacted for 4 hours at room temperature. The resulting materials were filtered, and the filter cake was washed with an appropriate amount of tetrahydrofuran. The filtrate was collected. To the filtrate was added 6 g of sodium borohydride, and then 3 mL of water was slowly added dropwise with dropping funnel within 1 hour. The reaction was run and monitored with TLC. After the reaction was completed, 50 mL of water was added to the reaction system. The solvent was evaporated under reduced pressure. The aqueous layer was extracted with ethyl acetate (40 mL×4). The organic layers were combined, and washed with 50 mL of 0.5 N hydrochloric acid, saturated sodium chloride aqueous solution and water, respectively. The mixture was dried with anhydrous sodium sulfate. The solvent was evaporated under reduced pressure to give a white solid crude product, to which was washed with ethyl acetate to give NM-009a as a white solid (1.43 g, 63.8%). ESI-MS: m/z 247.2 ([M+Na]$^+$). $^1$H-NMR (DMSO-d6, ppm): 1.21-1.26 (m, 6H), 1.33-1.45 (m, 4H), 1.54 (m, 2H), 1.93 (m, 2H), 3.40-3.47 (m, 4H), 4.20 (t, 2H, J=5.5 Hz).

Example 26. Synthesis of Compound NM-009b

In a 25 mL round-bottomed flask were added a white solid of compounds NM-009a (1.12 g, 5 mmol) and 5 mL of acetic anhydride with stirring. Then 2-3 drops (catalytic amount) perchloric acid was added into the suspension. The reaction was run at room temperature for 3 hours. The reaction solution was poured into 20 g of ice water, and extracted with ethyl acetate (20 mL×3). The organic layers were combined, and washed with 30 mL of 1 N sodium bicarbonate solution and 30 mL of water, and dried with anhydrous sodium sulfate. The solvent was evaporated under reduced pressure to give a crude product as a colorless oil, which was separated by silica column chromatography (petroleum ether:ethyl acetate=10:1) to obtain NM-009b as a colorless oil (1.43 g, 92.9%). ESI-MS: m/z 309.3 ([M+H$_2$O]$^+$). $^1$H-NMR (DMSO-d6, ppm): 1.25 (s, 2H), 1.35-1.47 (m, 12H), 1.55 (s, 2H), 1.98 (s, 8H), 4.04 (t, 4H).

Example 27. Synthesis of Compound NM-009c

Compound NM-009b (616 mg, 2 mmol) was placed in a 25 mL round-bottom flask, and cooled with an ice bath. Then 0.4 mL of concentrated nitric acid was added with stirring, and 2.5 mL of concentrated sulfuric acid was slowly added dropwise to the mixture. The reaction was run with an ice bath for 1 hour. Then 2 mL of acetonitrile (4.8 mmol) was slowly added dropwise, and cooled with an ice bath for 1 hour. The reaction mixture was poured into 20 mL of ice water, and the aqueous layers were extracted with ethyl acetate (20 mL×4). The organic layers were combined, and washed with 30 mL of 1 N sodium bicarbonate solution and 30 mL of water, and dried with anhydrous sodium sulfate. The solvent was evaporated under reduced pressure to give a crude product as colorless oil, which was separated by silica column chromatography (petroleum ether:ethyl acetate=1:3) to obtain compound NM-009c as an oil (423 mg, 57.9%). ESI-MS: m/z 366.3 ([M+H]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 28. Synthesis of Compound NM-009d

To a 100 mL round-bottom flask were added in order the compound NM-009c (1 g, 2.7 mmol), 1.5 g of solid sodium hydroxide and 30 mL of diethylene glycol. The reaction was run for 15 hours under 170° C. The mixture was cooled to room temperature. Then 20 mL of water and ethyl acetate (20 mL×3) were added in order to extract to remove impurities. Water was distilled off under reduced pressure. To the remaining solution were added 30 mL of tetrahydrofuran, 1.18 g of Boc anhydride (5.4 mmol), 540 mg of triethylamine (5.4 mmol) and 10 mg of DMAP. The reaction was run under room temperature for 5 hours, and monitored with TLC. After the reaction being completed, 20 mL of saturated ammonium chloride solution was added into the reaction solution, and the mixture was extracted with ethyl acetate (30 mL×4). The ethyl acetate layers were combined, and washed with 30 mL of water and saturated sodium chloride solution in order, and dried with anhydrous sulfate sodium sulfate. The solvent was evaporated under reduced pressure to give crude product as a pale yellow oil, which was separated by silica column chromatography (petroleum ether:ethyl acetate=2:1) to obtain compound NM-009d as an oil (700 mg, 75.4%). ESI-MS: m/z 340.4 ([M+H]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 29. Synthesis of Compound NM-009e Vb

Compound NM-009d (680 mg, 2 mmol) was dissolved in 10 mL of anhydrous dichloromethane with an ice water. Then a 2 mL mixture of acetic anhydride and fuming nitric acid in a ratio of 3:2 by volume was added. The ice bath was maintained and the reaction was run for 10-15 minutes. The reacted solution was poured into 10 mL of 1 N sodium bicarbonate solution. The dichloromethane was separated, and the aqueous layer was extracted with dichloromethane (10 mL×3). Organic layers were combined, washed with 10 mL of water, and dried with anhydrous sodium sulfate. The resulting materials were filtered, and the filtrate was distilled under reduced pressure to obtain a crude product as a colorless oil, which was separated by silica column chromatography (petroleum ether:dichloromethane=10:1) to give a product NM-009e as a colorless oil (620 mg, 72.3%). ESI-MS: m/z 452.1 [M+Na]. $^1$H NMR (300 MHz, DMSO-d$_6$) δ 1.17-1.29 (q, J=12 Hz, 2H), 1.36 (s, 13H), 1.49-1.53 (t, J=6 Hz, 4H), 1.52-1.66 (dd, J=33 Hz, 12 Hz, 4H), 1.68 (m, 2H), 2.09 (m, 1H, CH), 4.53-4.58 (t, J=7.5 Hz, 4H, 2×CH$_2$O), 6.46 (s, 1H, NH).

Example 30. Synthesis of Compound NM-009

To the compound NM-008 g (401 mg, 1 mmol) was added 5 mL of ether solution saturated with hydrogen chloride. The reaction was run at room temperature and monitored with TCL. When the reaction was completed, a white solid was precipitated. After filtration, the white solid was washed by anhydrous ether to give a pure product which was dried to give NM-008 (380 mg, 65.5%). ESI-MS: m/z 255.1 ([M+H]$^+$). $^1$H-NMR (DMSO-d6, ppm): 1.38-1.54 (m, 6H), 1.60-1.77 (m, 6H), 2.27 (m, 1H), 4.32 (s, 4H), 8.27 (s, 3 M.

Example 31. Synthesis of Compound NM-011a

Compound 1,3-dibromo-adamantane (3 g, 10 mmol) was dissolved in 30 mL of toluene, and then 250 mg of AIBN (1.5 mmol), 7 g of tri-n-butyl tin (24 mmol), 3 g of ethyl acrylate (30 mmol) were added in order. The reaction was refluxed with at 110° C. under nitrogen for 3 hours. The reaction solution was cooled to room temperature and was poured into 30 mL of 0.2M aqueous ammonia. After being stirred fully, the organic layer was separated. The aqueous layers were extracted with ethyl acetate (20 mL×4). The organic layers were combined and washed with 30 mL of water and 30 mL of saturated sodium chloride solution. The resulting materials were dried with anhydrous sodium sulfate, and solvent was evaporated under the reduced pressure to give a crude product as a colorless oil, which was separated by silica column chromatography (petroleum ether:ethyl acetate=10:1) to give compound NM-011a as a colorless oil (2 g, 46.6%). ESI-MS: m/z 337.4 ([M+H]$^+$). $^1$H-NMR (DMSO-d6, ppm): 1.11 (s, 2H), 1.15-1.19 (m, 6H), 1.28-1.39 (m, 12H), 1.53 (s, 2H), 1.97 (s, 2H), 2.19-2.24 (m, 2H), 4.03 (q, 4H, J=7.1 Hz).

Example 32. Synthesis of Compound NM-011b

Compound NM-011a (2.2 g, 6 mmol) was placed in a 50 mL round-bottom flask and cooled with an ice bath. Then 1.2 mL of concentrated nitric acid was added with stirring. To the mixture was slowly added dropwise 8.5 mL of concentrated sulfuric acid. The reaction was run for 1 hour cooled with an ice bath. To the reaction solution was slowly added 5.6 mL of acetonitrile (13.4 mmol). The reaction was continued with an ice bath for 1 hour. The reaction solution was poured to 20 mL of ice water, and the aqueous layer was extracted with ethyl acetate (20 mL×4). The organic layers were combined, and washed with 30 mL of 1 N sodium bicarbonate solution and 30 mL of water, and dried with anhydrous sodium sulfate. The solvent was evaporated under the reduced pressure to give a crude product as a colorless oil, which was separated by silica column chromatography (petroleum ether:ethyl acetate=1:3) to obtain compound NM-011b as an oil (2 g, 57.9%). ESI-MS: m/z 394.2 ([M+H]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 33. Synthesis of Compound NM-011c

Compound NM-011b (1 g, 2.5 mmol) was dissolved in 20 mL of dehydrate tetrahydrofuran, and 450 mg of sodium borohydride was added. Then, 1.33 g of aluminum chloride was dissolved in 10 mL of tetrahydrofuran, and the solution was slowly added dropwise into the reaction mixture. Then the reaction was stirred at room temperature overnight. The reaction solution was poured into 50 mL of ice-water, stirred fully, and extracted with ethyl acetate (30 mL×4). The organic layers were combined, washed with 30 mL of saturated sodium chloride, and dried with anhydrous sodium sulfate. The solvent was evaporated to dryness under reduced pressure to give a crude product as a colorless oil, which was separated by silica column chromatography (ethyl acetate:methanol=10:1) to obtain NM-011c as a colorless oil (470 mg, 60.8%). ESI-MS: m/z 310.1 ([M+H]$^+$). $^1$H-NMR (DMSO-d6, ppm): 1.05-1.09 (m, 6 H), 1.22-1.39 (m, 8H), 1.51-1.60 (m, 4H), 1.73 (s, 3H), 1.76 (s, 2H), 2.07 (m, 1H), 3.30-3.36 (m, 4H), 4.39 (t, 2H, J=5.2 Hz), 7.36 (s, 1H).

Example 34. Synthesis of Compound NM-011d

In 50 mL round-bottom flask were added in order a compound NM-011c (440 mg, 1.4 mmol), 750 mg of solid sodium hydroxide, and 10 mL of diethylene glycol. The reaction was run at 170° C. for 15 hours. The mixture was cooled to room temperature, and 20 mL of water was added. After being extracted with ethyl acetate (20 mL×3) to remove impurities, the water was removed by rotavap under reduced pressure. To the remaining solution were added 30 mL of tetrahydrofuran 560 mg of Boc anhydride (2.8 mmol), 280 mg of triethylamine (2.8 mmol), and 10 mg of DMAP. The reaction was run at room temperature for 5 hours, and monitored with TLC. After the reaction being completed, 20 mL of saturated ammonium chloride solution was added to the reaction solution, extracted with ethyl acetate (30 mL×4). The organic layers were combined, washed with 30 mL of water and saturated sodium chloride solution, and dried with anhydrous sulfate sodium sulfate. The solvent was evaporated under reduced pressure to give crude product as a pale yellow oil, which was separated by silica column chromatography (petroleum ether:ethyl acetate=2:1) to obtain compound NM-011d as an oil (320 mg, 55.9%). ESI-MS: m/z 340.4 ([M+H]$^+$). $^1$H-NMR (DMSO-d6, ppm):

1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 35. Synthesis of Compound NM-011e

Compound NM-011d (680 mg, 2 mmol) was dissolved in 10 mL of anhydrate dichloromethane, and cooled with an ice bath. Then, 2 mL a solution of acetic anhydride and fuming nitric acid in a ratio of 3:2 by volume was added. With the ice bath, the reaction was run for 10-15 minutes. The reaction solution was poured into 10 mL of 1 N sodium bicarbonate solution. After the organic layer being separated, the aqueous layer was extracted with dichloromethane (10 mL×3). The organic layers were combined, and washed with 10 mL of water and dried with anhydrous over sodium sulfate. After being filtrated, the solvent was distilled under reduced pressure to give a crude product as a colorless oil, which was separated by silica column chromatography (petroleum ether:dichloromethane=10:1) to obtain NM-011e as a colorless oil (620 mg, 72.3%). ESI-MS: m/z 452.1 ([M+Na]$^+$). $^1$H-NMR (DMSO-d6, ppm): 1.37 (s, 9H), 1.40 (m, 6H), 1.60 (m, 2H), 1.72-1.82 (m, 4H), 2.17 (m, 1H), 4.23 (s, 4H), 6.66 (s, 1H).

Example 36. Synthesis of Compound NM-011

To compound NM-011e (401 mg, 1 mmol) was added 5 mL of saturated solution of hydrogen chloride in ether. The reaction was run at room temperature, and monitored with TLC. After the reaction being completed, a white solid was precipitated. After filtration, the white solid was washed with anhydrous ether to give pure NM-011, which was dried to give NM-011 (380 mg, 65.5%). ESI-MS: m/z 255.1 ([M+H]$^+$). $^1$H-NMR (DMSO-d6, ppm): 1.38-1.54 (m, 6H), 1.60-1.77 (m, 6H), 2.27 (m, 1H), 4.32 (s, 4H), 8.27 (s, 3H).

Example 37. Synthesis of Compound NM-012a

A compound of 1,3-dibromo-adamantane (3 g, 10 mmol) was dissolved in 30 mL of toluene, and then 250 mg of AIBN (1.5 mmol), 7 g of tri-n-butyl tin (24 mmol), 3 g of 2-ethyl methacrylate were added in order. The reaction was refluxed at 110° C. under nitrogen for 3 hours. The reaction solution was cooled to room temperature, and was poured into 30 mL of 0.2 M aqueous ammonia. After being stirred fully, the organic layer was separated, the aqueous layer was extracted with ethyl acetate (20 mL×4). The organic layers were combined, and washed with 30 mL of water and 30 mL of saturated sodium chloride solution, dried with anhydrous sodium sulfate. The solvent was evaporated under reduced pressure to give a crude product as a colorless oil, which was separated by silica column chromatography (petroleum ether:ethyl acetate=10:1) to obtain NM-012a as a colorless oil (1.6 g, 43.1%). ESI-MS: m/z 337.4 ([M+H]$^+$). $^1$H-NMR (DMSO-d6, ppm): 0.97 (s, 2H), 1.02-1.08 (m, 8H), 1.15-1.20 (m, 7H), 1.22-1.40 (m, 7H), 1.50 (s, 2H), 1.57-1.65 (m, 2H), 1.93 (s, 2H), 2.39-2.47 (m, 2H), 3.98-4.11 (m, 4H).

Example 38. Synthesis of Compound NM-012b

Compound NM-012a (2 g, 5.5 mmol) was dissolved in 50 mL round-bottom flask, and cooled with an ice bath. Then, 1.1 mL of concentrated nitric acid was added with stirring. To the reaction mixture was slowly added dropwise 7.7 mL of concentrated sulfuric acid. The reaction was run with an ice bath for 1 hour. Then 4.9 mL of acetonitrile (11.7 mmol) was slowly added dropwise and the reaction was continued with the ice bath for 1 hour. The reaction solution was poured into 20 mL into ice water. The aqueous layer was extracted with ethyl acetate (20 mL×4). The organic layers were combined, and washed with 30 mL of 1 N sodium bicarbonate solution and 30 mL of water, and dried with anhydrous sodium sulfate. The solvent was evaporated to dryness under reduced pressure to give a crude product as a colorless oil, which was separated by silica column chromatography (petroleum ether:ethyl acetate=1:3) to obtain compound NM-011b as an oil (1.6 g, 69.2%). ESI-MS: m/z 422.2 ([M+H]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 39. Synthesis of Compound NM-012c

Compound NM-012b (2 g, 4.7 mmol) was dissolved in 30 mL of anhydrate tetrahydrofuran, and 900 mg of sodium borohydride was added. Then, 2.6 g of aluminum chloride was dissolved in 20 mL of tetrahydrofuran, which was slowly added dropwise into the reaction materials. Then the mixture was stirred at room temperature overnight. The reaction solution was poured into 50 mL of ice water, stirred fully, and extracted with ethyl acetate (30 mL×4). The extracts were combined, and washed with 30 mL of saturated sodium chloride, and dried with anhydrous sodium sulfate. The solvent was evaporated to dryness under reduced pressure to give a crude product as a colorless oil, which was separated by silica column chromatography (ethyl acetate:methanol=10:1) to obtain NM-012c as a colorless oil (880 mg, 55.6%). ESI-MS: m/z 338.1 ([M+H]$^+$). $^1$H-NMR (DMSO-d6, ppm): 1.05-1.09 (m, 6H), 1.22-1.39 (m, 8H), 1.51-1.60 (m, 4H), 1.73 (s, 3H), 1.76 (s, 2H), 2.07 (m, 1H), 3.30-3.36 (m, 4H), 4.39 (t, 2H, J=5.2 Hz), 7.36 (s, 1H).

Example 40. Synthesis of Compound NM-012d

In 50 mL round-bottom flask were added in order compound NM-012c (670 mg, 2 mmol), 1 g of solid sodium hydroxide and 10 mL of diethylene glycol. The reaction was run at 170° C. for 15 hours. The reaction was cooled to room temperature, and 20 mL of water was added. The resulting materials were extracted with ethyl acetate (20 mL×3), and evaporated to remove water under reduced pressure. Then, 30 mL of tetrahydrofuran, 900 mg of Boc anhydride (4 mmol), 400 mg of triethylamine (4 mmol) and 10 mg of DMAP were added to the remaining solution, and reacted for 5 hours and monitored with TLC. After the reaction being completed, 20 mL of saturated ammonium chloride solution was added to the reaction solution, and extracted with ethyl acetate (30 mL×4). The ethyl acetate layers were combined, and washed with 30 mL of water and saturated sodium chloride solution in order, and dried with anhydrous sulfate sodium sulfate. The solvent was evaporated under reduced pressure to give crude product as a pale yellow oil, which was separated by silica column chromatography (petroleum ether:ethyl acetate=2:1) to obtain compound NM-012d as an oil (500 mg, 63.3%). ESI-MS: m/z 340.4 ([M+H]$^+$). $^1$H-NMR (DMSO-d6, ppm): 1.22-1.43 (m, 6H), 1.67 (s, 4H), 1.74 (s, 3H), 1.81 (s, 2H), 2.02 (s, 6H), 2.15 (m, 1H), 3.70 (s, 4H).

Example 41. Synthesis of Compound NM-012e

Compound NM-012d (680 mg, 2 mmol) was dissolved in 10 mL of anhydrate dichloromethane, cooling with an ice bath, and 2 mL of solution of acetic anhydride and fuming nitric acid in a ratio of 3:2 by volume was added. The ice bath was maintained, and the reaction was run for 10-15 minutes. The reaction solution was poured into 10 mL of 1 N sodium bicarbonate solution. The organic phase was separated and the aqueous layer was extracted with dichloromethane (10 mL×3). The organic layers were combined and washed with 10 mL of water, and dried with anhydrous sodium sulfate. After filtration, the solvent was distilled under reduced pressure to obtain a crude product as a colorless oil, which was separated by silica column chromatography (petroleum ether:dichloromethane=10:1) to give NM-012e as a colorless oil (620 mg, 72.3%). ESI-MS: m/z 508.1 [M+Na]$^+$. $^1$H NMR (300 MHz, DMSO-d$_6$) 50.93-0.96 (d, J=9 Hz, 2×CH$_3$), 0.95-1.01 (dd, J=15 Hz, 6 Hz, 2H), 1.13 (m, 2H), 1.18-1.20 (d, J=6 Hz, 1H), 1.22-1.24 (d, J=6 Hz, 1H), 1.30 (s, 4H), 1.36 (s, 9H, C(CH$_3$)$_3$), 1.48-1.56 (m, 4H), 1.70 (m, 2H), 1.93-1.99 (m, 2H), 2.07 (m, 1H), 4.21-4.36 (m, 4H, 2×CH$_2$O), 6.41 (s, 1H, NH).

Example 42. Synthesis of Compound NM-012

A 5 mL solution of saturated hydrogen chloride in ether was added into compound NM-011e (401 mg, 1 mmol). The reaction was run at room temperature, and monitored with TLC. A white solid was precipitated after the reaction being completed. After filtration, the white solid was washed with anhydrous ether to give a pure NM-011, which was dried to give NM-011 (380 mg, 65.5%). ESI-MS: m/z 255.1 ([M+H]). $^1$H-NMR (DMSO-d6, ppm): 1.38-1.54 (m, 6H), 1.60-1.77 (m, 6H), 2.27 (m, 1H), 4.32 (s, 4H), 8.27 (s, 3H).

Example 43. Protective Effects of Compounds on Primary Cerebellum Granule Cells of Rats Isolated primary cerebellum granule cells of infant rats were inoculated in 96-well plates with 1.2×10$^5$/well by using 10% FBS+25 mM KCl+2 mM Glutamine+1% of double-antibody BME medium. After 24 hours, cytarabine with a final concentration of 10 iM was added to inhibit the proliferation of neurogliocyte cells. After the day 4, glucose with the final concentration of 5 mM was added every four days to complement energy metabolism and water evaporation of cells. The materials were placed in a cell incubator (37° C., 5% CO$_2$) to be cultured for 10 days. A 200 iM of glutamate was used to induce the excitotoxic injury of the primary cerebellum granule cells, with test groups of normal control group, glutamate group, pretreatment groups with different memantine nitrate compounds, and pretreatment control group with memantine. In the testing groups, the compounds of NM-001, NM-002, NM-003, NM-004, NM-005, NM-008, NM-009, NM-011, NM-012 and memantine were respectively added. After pre-protection for 2 h, 200 iM of glutamate was added to induce cell damage for 24 h, and then MTT was added to culture for 4 h. The supernatant fraction was sucked, and 150 iL of DMSO was added to each well for dissolving. After blending with shaking, the light absorption values under 570 nm wavelength was measured with a microplate reader, and the viability of cells was calculated. Cell viability (%)=absorbance of different groups/absorbance of the normal control group×100%.

TABLE 1

Protective effects of the compounds on rat's nerve cells

| Compounds | EC$_{50}$ (μM) |
|---|---|
| NM-001 | 24.62 |
| NM-002 | 25.2 |
| NM-003 | 15.36 |
| NM-004 | 8.12 |
| NM-005 | 6.06 |
| NM-008 | 4.37 |
| NM-009 | 5.20 |
| NM-011 | 5.86 |
| NM-012 | 9.30 |
| YQW-036 | 31.4 |
| memantine | 2.72 |

Example 44. Protective Effect of the Compound NM-008 in a Rat Cerebral Ischemia MCAo Model Female SD rats weighted 280-295 g were anesthetized with isoflurane, the proximal end of cephalic artery and the external carotid artery were ligatured separately, and a line embolism was inserted from the cephalic artery into the internal carotid carotid. After insertion of the line embolism, the changes of the local cerebral blood flow were measured with a blood flow-meter. Before the preparation of the model and 5 min after the embolization, the flow change of the right ischemic area was measured by using a laser Doppler flow-meter, the criteria of success being that, after the embolism, blood flow is reduced to lower than 60 percent of the normal value.

Figure 8:
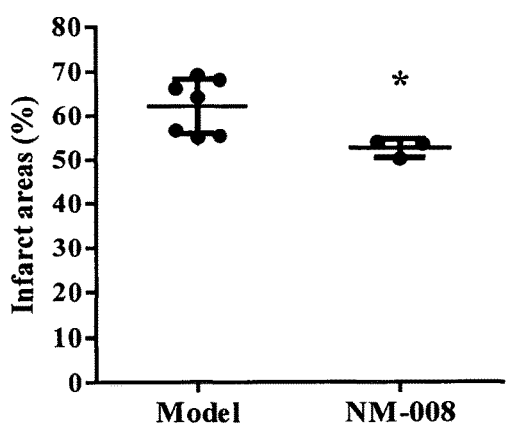
FIG. 8 illustrates the protective effect of the compound NM-008 to cerebral infarction of rats of a permanent cerebral ischemia model, while "*" indicates a significant difference compared with a control group.

At the time 3 h and 6 h after the model being prepared successfully, the rats was injected with the drug (60 mg/kg) intravenously once. Then, 24 h after the model being prepared, the animal was anesthetized with pentobarbital sodium, and was decapitated to give brain slices, which were stained with TTC to calculate the infarct area. It is shown that, as compared with the model group, NM-008 significantly reduced infarct area in the stoke model (P<0.05), and the protection ratio was 15.3% (FIG. 8).

The invention claimed is:

1. An amantadine nitrate compound with neural protective effects, having a structure of formula (II):

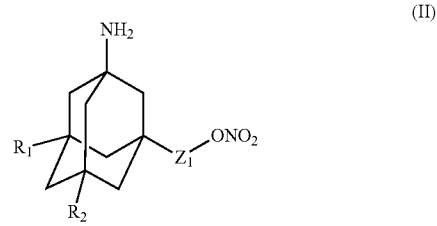

(II)

or a pharmaceutically acceptable salt thereof,
wherein R$_2$ is hydrogen, R$_1$ is a straight-chain or branched-chain alkyl, and number of carbon atoms contained in Z$_1$ and R$_1$ together is no less than 3.

2. An amantadine nitrate compound with neural protective effects, having a structure of formula (III):

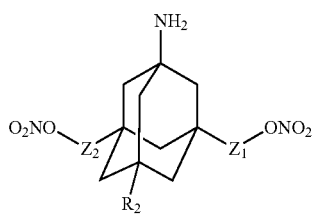

(III)

or a pharmaceutically acceptable salt thereof,
wherein:
- $R_2$ is hydrogen, straight-chain or branched-chain or cyclic alkyl, optionally substituted-aryl or heteroaryl, or contains a nitrate ester group;
- $Z_1$ and $Z_2$ are each independently a straight- or branched-carbon chain connecting to a nitrate ester group, wherein $Z_1$ and $Z_2$ each independently can be substituted with heteroatom, alkyl, aryl and heteroaryl, and $Z_1$ and $Z_2$ each independently have 1-6 carbon atoms;
- wherein, the alkyl has up to 10 carbon atoms, the cyclic alkyl is cyclopropyl, cyclobutyl, cyclopentyl or cyclohexyl; a substituent is $N(CH_3)_2$, F, Cl, Br, I, $OCH_3$, $CO_2CH_3$, CN, aryl or heteroaryl; the aryl is monocyclic aryl, and the heteroaryl is monocyclic heteroaryl.

3. The compound of claim 2, selected from the group consisting of:

NM-008

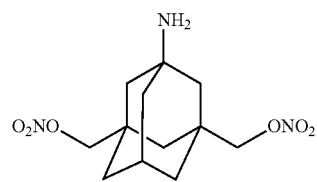

NM-009

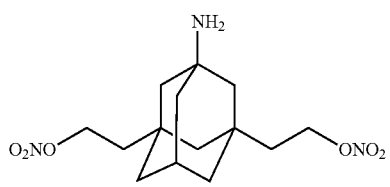

NM-010

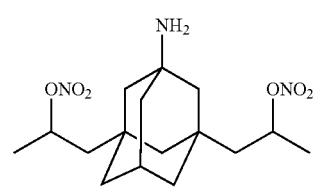

NM-011

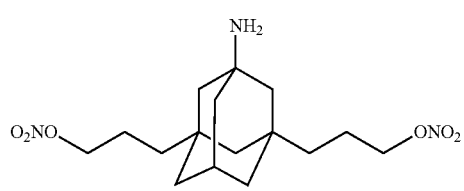

NM-012

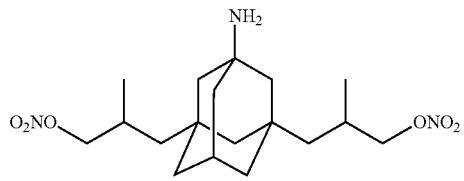

4. The compound of claim 2, wherein $R_2$ contains a nitrate ester group, and thus the compounds have a structure of formula (IV):

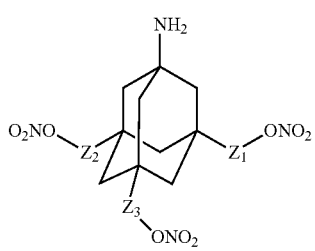

(IV)

wherein:
- $Z_1$, $Z_2$ and $Z_3$ are each independently a straight- or branched-carbon chain connecting to a nitrate ester group of $R_1$, $R_2$ and $R_3$ respectively, wherein $Z_1$, $Z_2$ and $Z_3$ each independently can be substituted with heteroatom, alkyl, aryl and heteroaryl, and $Z_1$, $Z_2$ and $Z_3$ independently have 1-6 carbon atoms;
- wherein, the alkyl has up to 10 carbon atoms, the cyclic alkyl is cyclopropyl, cyclobutyl, cyclopentyl or cyclohexyl; a substituent is $N(CH_3)_2$, F, Cl, Br, I, $OCH_3$, $CO_2CH_3$, CN, aryl or heteroaryl; the aryl is monocyclic aryl, and the heteroaryl is monocyclic heteroaryl.

5. A method for preparation of the compound of claim 1 or 2, comprising: using starting materials of adamantine optionally substituted with bromo, alkyl or alkyl carboxylic group, introducing a amino group via Ritter reaction, and then forming a nitrate ester group on a substituted side chain of the amantadine via esterification of a hydroxy attached on adamantyl ring by using fuming nitric acid.

6. The compound of claim 1, selected from the group consisting of:

NM-004

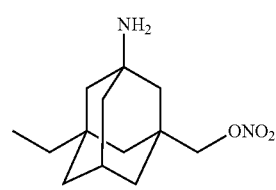

NM-005

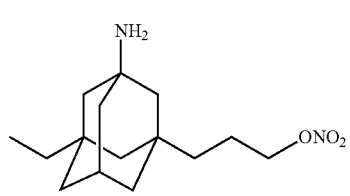

NM-006
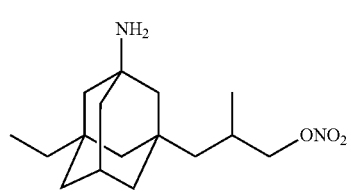
NM-007
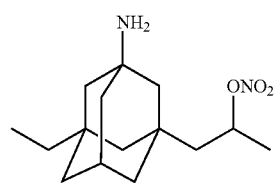
or a pharmaceutically acceptable salt thereof.
* * * * *